United States Patent [19]

Pierce et al.

[11] Patent Number: 5,300,431
[45] Date of Patent: Apr. 5, 1994

[54] POSITIVE SELECTION VECTOR FOR THE BACTERIOPHAGE P1 CLONING SYSTEM

[75] Inventors: James C. Pierce, Wilmington, Del.; Nat L. Sternberg, West Chester, Pa.

[73] Assignee: E. I. Du Pont de Nemours and Company, Wilmington, Del.

[21] Appl. No.: 662,224

[22] Filed: Feb. 26, 1991

[51] Int. Cl.$^5$ .................. C12N 15/00; C12N 1/21; C12N 15/70; C12N 15/11
[52] U.S. Cl. .................. 435/172.3; 435/320.1; 435/252.33; 935/79; 935/83; 935/84; 536/23.2; 536/24.1
[58] Field of Search .................. 536/27, 23.7, 23.2, 536/24.1; 435/34, 38, 252.3, 252.33, 177.3, 320.1; 935/9, 72, 73, 79, 83, 84

[56] References Cited

U.S. PATENT DOCUMENTS 4,766,072 8/1988 Jendrisak et al. .................. 435/91

FOREIGN PATENT DOCUMENTS 0117823 5/1984 European Pat. Off. ...... C12N 15/00

OTHER PUBLICATIONS

Sternberg, Proc. Natl. Acad. Sci. USA, 87:103-107 (1990).
Collins et al., Gene, 4:85-107 (1978).
Collins, et al., Proc. Natl. Acad. Sci. USA, 75:4242-4246 (1978).
Burke, et al, Science, 236:806-812 (1987).
Sternberg, et al., The New Biol., 2:151-162 (1990).
Henrich, et al., Gene, 42:345-349 (1986).
Kuhn, et al., Gene, 42:253-263 (1986).
Burns, et al., Gene, 27:323-325 (1984).
Gay, et al., J. Bacteriol., 164:918-921 (1985).
Gay, et al., J. Bacteriol., 153:1424-1431 (1983).
Stevis et al., Gene vol. 55, 1987, Elsevier Publishers, N.Y., U.S.; pp. 67-74.
J. L. Eliason et al., J. Molecular Biology, 198(2):281 (1987).
Osborne, F. A. et al. 1989, Nucleic Acids Res. vol. 17, pp. 7671-7680.
Honigman, A. et al. 1981, Gene vol. 13, pp. 289-298.
Dreiseikelmann, B. et al. 1988, J. Biol. Chem. vol. 263, pp. 1391-1397.
Rossi, J. J. et al. 1983, Proc. Natl. Acad. Sci. USA vol. 80, pp. 3203-3207.
Tang, L. B. et al. 1990, Gene vol. 96, pp. 89-93.
Sternberg, N. L. 1990 Gen. Arct. Tech. Appl. vol. 7, pp. 126-132.
Kaniga, K. et al. 1991, Gene vol. 109, pp. 137-141.
Ried, J. L. et al. 1987, Gene vol. 57, pp. 239-246.

Primary Examiner—Richard A. Schwartz
Assistant Examiner—Mary E. Mosher
Attorney, Agent, or Firm—R. Thomas Gallegos

[57] ABSTRACT

Positive selection cassettes are disclosed which contain a lethal gene, a promoter, a repressor sequence overlapping the promoter, and a cloning site between the promoter and the lethal gene. Insertion of a foreign nucleic acid sequence into the cloning site prevents expression of the lethal gene. Expression of the lethal gene under nonrepressed conditions kills a host organism containing a positive selection cassette which does not contain the foreign nucleic acid sequence.

5 Claims, 5 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 52 bases
        ( B ) TYPE: nucleic acid
        ( C ) STRANDEDNESS: single
        ( D ) TOPOLOGY: linear ( i i ) MOLECULE TYPE: synthetic oligonucleotide ( i i i ) HYPOTHETICAL: NO ( i v ) ANTI-SENSE: NO ( v ) ORIGINAL SOURCE:
    ( A ) ORGANISM: not applicable
    ( B ) STRAIN: not applicable
    ( C ) CELL TYPE: not applicable ( v i ) IMMEDIATE SOURCE:
    ( A ) LIBRARY: not applicable
    ( B ) CLONE: not applicable ( x ) PUBLICATION INFORMATION:

( x i ) SEQUENCE DESCRIPTION: SEQ ID NO:1:

TCGAGCTTGA CATTGTAGGA CTATATTGCT CTAATAAATT TGCGGCCGCT TG    52

( 2 ) INFORMATION FOR SEQ ID NO:2:

( i ) SEQUENCE CHARACTERISTICS:
        ( A ) LENGTH: 52 bases
        ( B ) TYPE: nucleic acid
        ( C ) STRANDEDNESS: single
        ( D ) TOPOLOGY: linear ( i i ) MOLECULE TYPE: synthetic oligonucleotide ( i i i ) HYPOTHETICAL: NO ( i v ) ANTI-SENSE: NO ( v ) ORIGINAL SOURCE:
        ( A ) ORGANISM: not applicable
        ( B ) STRAIN: not applicable
        ( C ) CELL TYPE: not applicable ( v i ) IMMEDIATE SOURCE:
        ( A ) LIBRARY: not applicable
        ( B ) CLONE: not applicable ( x ) PUBLICATION INFORMATION:

( x i ) SEQUENCE DESCRIPTION: SEQ ID NO:2:

GATCCAAGCG GCCGCAAATT TATTAGAGCA ATATAGTCCT ACAATGTCAA GC    52

( 2 ) INFORMATION FOR SEQ ID NO:3:

( i ) SEQUENCE CHARACTERISTICS:
        ( A ) LENGTH: 37 bases
        ( B ) TYPE: nucleic acid
        ( C ) STRANDEDNESS: single
        ( D ) TOPOLOGY: linear ( i i ) MOLECULE TYPE: synthetic oligonucleotide ( i i i ) HYPOTHETICAL: NO ( i v ) ANTI-SENSE: NO ( v ) ORIGINAL SOURCE:
        ( A ) ORGANISM: not applicable
        ( B ) STRAIN: not applicable
        ( C ) CELL TYPE: not applicable ( v i ) IMMEDIATE SOURCE:
        ( A ) LIBRARY: not applicable
        ( B ) CLONE: not applicable ( x ) PUBLICATION INFORMATION:

( x i ) SEQUENCE DESCRIPTION: SEQ ID NO:3:

GGCCGCGGAT CCGTCGACGG CCAATTAGGC CTACGTA    37

( 2 ) INFORMATION FOR SEQ ID NO:4:

( i ) SEQUENCE CHARACTERISTICS:
        ( A ) LENGTH: 37 bases

```
            ( B ) TYPE: nucleic acid
            ( C ) STRANDEDNESS: single
            ( D ) TOPOLOGY: linear ( i i ) MOLECULE TYPE: synthetic oligonucleotide ( i i i ) HYPOTHETICAL: NO ( i v ) ANTI-SENSE: NO ( v ) ORIGINAL SOURCE:
            ( A ) ORGANISM: not applicable
            ( B ) STRAIN: not applicable
            ( C ) CELL TYPE: not applicable ( v i ) IMMEDIATE SOURCE:
            ( A ) LIBRARY: not applicable
            ( B ) CLONE: not applicable ( x ) PUBLICATION INFORMATION:

( x i ) SEQUENCE DESCRIPTION: SEQ ID NO:4:

GATCTACGTA  GGCCTAATTG  GCCGTCGACG  GATCCGC       37

( 2 ) INFORMATION FOR SEQ ID NO:5:

( i ) SEQUENCE CHARACTERISTICS:
            ( A ) LENGTH: 9 bases
            ( B ) TYPE: nucleic acid
            ( C ) STRANDEDNESS: single
            ( D ) TOPOLOGY: linear ( i i ) MOLECULE TYPE: synthetic oligonucleotide ( i i i ) HYPOTHETICAL: NO ( i v ) ANTI-SENSE: NO ( v ) ORIGINAL SOURCE:
            ( A ) ORGANISM: not applicable
            ( B ) STRAIN: not applicable
            ( C ) CELL TYPE: not applicable ( v i ) IMMEDIATE SOURCE:
            ( A ) LIBRARY: not applicable
            ( B ) CLONE: not applicable ( x ) PUBLICATION INFORMATION:

( x i ) SEQUENCE DESCRIPTION: SEQ ID NO:5:

CCACTAGTC       9

( 2 ) INFORMATION FOR SEQ ID NO:6:

( i ) SEQUENCE CHARACTERISTICS:
            ( A ) LENGTH: 13 bases
            ( B ) TYPE: nucleic acid
            ( C ) STRANDEDNESS: single
            ( D ) TOPOLOGY: linear ( i i ) MOLECULE TYPE: synthetic oligonucleotide ( i i i ) HYPOTHETICAL: NO ( i v ) ANTI-SENSE: NO ( v ) ORIGINAL SOURCE:
            ( A ) ORGANISM: not applicable
            ( B ) STRAIN: not applicable
            ( C ) CELL TYPE: not applicable ( v i ) IMMEDIATE SOURCE:
            ( A ) LIBRARY: not applicable
            ( B ) CLONE: not applicable ( x ) PUBLICATION INFORMATION:

( x i ) SEQUENCE DESCRIPTION: SEQ ID NO:6:
```

AATTGACTAG TGG    13

( 2 ) INFORMATION FOR SEQ ID NO:7:

( i ) SEQUENCE CHARACTERISTICS:
        ( A ) LENGTH: 56 bases
        ( B ) TYPE: nucleic acid
        ( C ) STRANDEDNESS: single
        ( D ) TOPOLOGY: linear ( i i ) MOLECULE TYPE: synthetic oligonucleotide ( i i i ) HYPOTHETICAL: NO ( i v ) ANTI-SENSE: NO ( v ) ORIGINAL SOURCE:
        ( A ) ORGANISM: not applicable
        ( B ) STRAIN: not applicable
        ( C ) CELL TYPE: not applicable ( v i ) IMMEDIATE SOURCE:
        ( A ) LIBRARY: not applicable
        ( B ) CLONE: not applicable ( x ) PUBLICATION INFORMATION:

( x i ) SEQUENCE DESCRIPTION: SEQ ID NO:7:

GGCCGCTAAT ACGACTCACT ATAGGGAGAG GATCCTTCTA TAGTGTCACC TAAATG    56

( 2 ) INFORMATION FOR SEQ ID NO:8:

( i ) SEQUENCE CHARACTERISTICS:
        ( A ) LENGTH: 56 bases
        ( B ) TYPE: nucleic acid
        ( C ) STRANDEDNESS: single
        ( D ) TOPOLOGY: linear ( i i ) MOLECULE TYPE: synthetic oligonucleotide ( i i i ) HYPOTHETICAL: NO ( i v ) ANTI-SENSE: NO ( v ) ORIGINAL SOURCE:
        ( A ) ORGANISM: not applicable
        ( B ) STRAIN: not applicable
        ( C ) CELL TYPE: not applicable ( v i ) IMMEDIATE SOURCE:
        ( A ) LIBRARY: not applicable
        ( B ) CLONE: not applicable ( x ) PUBLICATION INFORMATION:

( x i ) SEQUENCE DESCRIPTION: SEQ ID NO:8:

TCGACATTTA GGTGACACTA TAGAAGGATC CTCTCCCTAT AGTGAGTCGT ATTAGC    56

POSITIVE SELECTION VECTOR FOR THE BACTERIOPHAGE P1 CLONING SYSTEM

FIELD OF THE INVENTION

This invention allows the selection of large molecular weight DNA inserts in the P1 cloning system by positive selection for the ability of clones with inserts to grow on media in the presence of sucrose. This new P1 vector also facilitates characterization of cloned DNA.

BACKGROUND OF THE INVENTION

The bacteriophage P1 cloning system allows the headful in vitro packaging of foreign DNA fragments as large as 95 kb in length. Sternberg, Proc. Natl. Acad. Sci. USA 87, 103–107 (1990) has shown that the P1 cloning system can generate 100,000 clones containing inserts per microgram of vector DNA. Large molecular weight clones are faithfully replicated in E. coli host strains and DNA from these clones can be easily isolated by standard molecular biological techniques. Thus, the P1 cloning system rivals Yeast Artificial Chromosomes (YAC) and cosmid cloning systems for the generation and characterization of genomic libraries.

Cosmid cloning vectors were designed by Bruning et al., Gene 4, 85–107 (1978) and Collins et al., Proc. Natl. Acad. Sci. USA, 75, 4242–4246 (1978), so that a bacteriophage lambda in vitro packaging reaction can encapsulate insert DNA up to 47 kb and infect E. coli at high efficiency. The cosmid vector plus insert DNA is cyclized in the E. coli bacterium at the lambda cos sites located on the vector. The same cos site is used in recognition by the lambda packaging apparatus for encapsulation of the vector-insert DNA into the lambda bacteriophage head. A major limitation of the cosmid cloning system is the relatively small size of the insert clone (47 kb). Many eukaryotic genes have been shown to be larger than 50 kb with some genes (e.g., dystrophin) up to 1000 kb. The small size of cosmid clones necessitates a labor intensive and "error-prone" procedure of multiple chromosome "walking" and "jumping" methodologies when isolating large genomic clones.

Another system for cloning large molecular weight DNA fragments is Yeast Artificial Chromosomes (YAC's) developed by Burke et al., Science 236, 806–812 (1987). YAC cloning enables DNA inserts up to 1000 kb to be propagated as minichromosomes in specific yeast strains YAC vectors contain a yeast replication origin, a centromere, and a set of telomeres. After ligation of insert DNA to the YAC vector, the DNA is introduced into yeast spheroplasts by direct DNA transformation. The major limitation of YAC cloning is the inefficiency of the transformation reaction (about 1000 clones per microgram of vector DNA) and the difficulty in characterization of YAC clones once they have been generated. The YAC clone represents a small proportion (less than 1%) of the total DNA in a yeast cell. This makes recovery, isolation, and analysis of any particular YAC clone burdensome.

The bacteriophage P1 cloning system complements both cosmid and YAC cloning in the construction of genomic libraries. A 50,000-member human DNA library has been generated in the P1 cloning system by Sternberg et al., The New Biol. 2, 151–162 (1990) which represents about a one times coverage of the human genome. The most recent P1 cloning vector (pNS582tet14Ad10) consists of a P1 pac site used for the initiation of headful packaging, two P1 lox sites which cyclize the P1 vector upon introduction in an E. coli host strain containing the P1 cre protein, a kanamycin gene for determining which E. coli cells contain a P1 plasmid, and a tetracycline gene for the cloning of insert DNA. The P1 cloning vector also contains a bacteriophage P1 plasmid replicon which maintains the P1 clone at a single copy per cell, and an IPTG inducible P1 lytic replicon for amplifying P1 clones in DNA isolation procedures. Another aspect of the cloning vector is a 10 kb "stuffer fragment" from adenovirus DNA which gives flexibility in the headful packaging reaction.

A model P1 cloning reaction consists of cutting the pNS582tet14Ad10 with the restriction enzymes ScaI and BamHI to generate 5 kb and 25 kb vector "arms". The digested vector DNA is then treated with calf intestine alkaline phospatase to inhibit self ligation of the vector. The vector arms are added to genomic DNA fragments that were previously digested with a BamHI-end compatible restriction enzyme (e.g. Sau3A). The two DNA's are then ligated and a portion of the ligation mixture is added to the first part of the two stage P1 in vitro packaging reaction. The first reaction consists of a cell extract prepared from P1 infected E. coli which is enriched for the P1 pac cleavage proteins. After pac cleavage, the DNA mixture is incubated in the stage II P1 in vitro packaging reaction which consists of a E. coli cell extract enriched for P1 virion capsids and tails. The phage encapsulated DNA is then infected into an E. coli host strain that contains the cre recombinase. A lox-lox site specific recombination reaction effectively cyclizes the P1 vector-insert clone which is maintained as a single copy extrachromosomal circular plasmid. To isolate DNA from a P1 clone, the cell containing the clone is grown in the presence of IPTG which induces the P1 lytic replicon. This induction increases the copy number of the P1 cone about 25 fold which gives enough DNA (about 1 microgram) from a 10 ml mini-alkaline lysis DNA isolation procedure for standard restriction mapping and size characterization procedures.

One problem encountered in the P1 cloning system is that a significant number of P1 vector molecules that contained no insert were present after a typical cloning experiment. These "no-insert" clones interfered with subsequent analysis of the cloning experiment in two ways. First, the number of clones to be screened when looking for a particular DNA insert was markedly increased due to the presence of "no-insert" containing clones. Secondly, upon subsequent growth of E. coli from a P1 cloning experiment, the bacteria that contained a "no-insert" vector generally grew much better than clones that contained large DNA inserts. Therefore, after a few rounds of growth the population of E. coli containing clones was greatly increased for "no-insert" vector clones.

To overcome the problems encountered in the previous versions of the P1 cloning system the pAd10-SacBII positive selection P1 cloning vector was developed. Many other positive selection based cloning systems have been developed for standard plasmid based recombinant DNA work. Henrich et. al., Gene 42, 345–349 (1986) demonstrated a positive selection vector based on the E gene (lysis protein) of bacteriophage φX174. Kuhn et al, Gene 42, 253–263 (1986) developed a system which uses the EcoRI endonuclease. Burns et. al., Gene 27, 323-325 (1984) showed that positive selection can be generated in a system based on resistance to 5-fluorouracil. Other similar systems are listed in the Burns et al. article.

Another positive selection system used in DNA cloning is based on the sacB gene from *Bacillus subtilis*. This gene codes for the enzyme levansucrase (sucrose:2,6-β-D-fructan 6-β-D fructosyltransferase; EC 2.4.1.10) which catalyzes the transfructorylation of sucrose to various acceptor substrates resulting in the hydrolysis of sucrose and levan synthesis. Gay et al., J. Bacteriol. 164, 918-921 (1985) demonstrated that the production of levansucrase in *E. coli* is lethal in the presence of growth media containing 5% sucrose. Gay et al. have used this knowledge to develop a positive selection cloning system based on inactivating the *B. subtilis sacB* structural gene. This allows the growth of only those *E. coli* bacteria containing recombinant clones that have DNA inserts when grown in the presence of sucrose.

Tang et. al., Gene (in press) (1990), (U.S. patent application Ser. No. 07/376,474) have cloned the sacB gene from *Bacillus amyloliouefaciens* and shown extensive DNA sequence homology to the sacB gene from *B. subtilis*. When the sacB gene from *B. amyloliouefaciens* was cloned on a multicopy plasmid in *E. coli*, a lethal phenotype is observed when cells are grown in the presence of sucrose. This knowledge has inspired us to develop a novel P1 positive selection cloning vector, pAd10-SacBII.

SUMMARY OF THE INVENTION

This invention describes a new bacteriophage P1 cloning vector (pAd10-SacBII) which allows for the positive selection of clones containing large molecular weight inserts. Improvements of the P1 cloning system are:

(a) a positive selection system based on the sacB gene from *Bacillus amylolicuefaciens* which codes for the enzyme levansucrase (sucrose:2,6-β-D-fructan 6-β-D fructosyltransferase; E.C.2.4.1.10). A unique promoter cassette has been invented which allows the disruption of sacB expression by cloning foreign DNA into a unique BamHI site between the promoter and sacB structural gene.

(b) a regulatory system based on the bacteriophage P1 c1 repressor protein to control the expression of the lethal sacB gene.

(c) an *E. coli* host strain that contains an integrated lambda phage that expresses the P1 c1 gene.

(d) placement of a bacteriophage T7 and Sp6 RNA polymerase promoters which border the cloning site of the P1 vector to facilitate characterization and analysis of P1 clones.

(e) placement of unique rare cutting restriction enzyme sites, SfiI SalI, and NotI which border the BamHI cloning site of the P1 vector to facilitate characterization and isolation of cloned foreign DNA inserts.

STATEMENT OF DEPOSIT

The following plasmids and bacteria relating to this invention have been deposited in the American Type Culture Collection, 12301 Parklawn Drive, Rockville, Md. 20852-1776 under the Budapest Treaty on Dec. 21, 1990.

pAd10-SacBII was designated ATCC Accession No. 68505.

pAd10-SacBI was designated ATCC Accession No. 68504.

NS3607 was designated ATCC Accession No. 55135.

DETAILED DESCRIPTION OF THE INVENTION

The vector described herein is an improvement to the P1 cloning system in the following manner:

(1) The pAd10-SacBII vector allows for the positive selection of large molecular weight DNA clones by killing clones that do not have a DNA insert when bacteria containing the clone are grown on media supplemented with sucrose.

(2) Analysis of large molecular weight clones is facilitated by the ability to remove the vector DNA fragment away from the clone insert by cutting with the restriction enzymes NotI and SfiI or SalI which are unique to the vector and directly border the unique BamHI site used in cloning.

(3) Chromosomal "walking" and "jumping" procedures will be greatly improved by the ability to make RNA and DNA probes from both ends of the DNA insert by using the bacteriophage T7 and Sp6 promoters that border the unique BamHI site.

(4) DNA sequence information from both ends of the cloned DNA insert will be readily obtained by using the unique bacteriophage T7 and Sp6 promoters as sites for DNA sequencing primers. This sequence information can then be reported as Sequence Tagged Sites (STS) for each P1 clone.

Construction of the pAd10-SacBII Vector

Construction of the P1 positive selection cloning vector (pAd10-SacBII) was initiated by cutting the parent P1 vector pNS582tet14Ad10 (FIG. 1), The New Biol. 2, 151-162 (1990), available from New England Nuclear as NENPHAGE®, with the restriction enzymes SalI and BamHI. This removed a 276 base pair fragment from the tetracycline gene of the parent vector. A synthetic duplex DNA oligonucleotide (promoter cassette) Lewin, B. (1983) Genes. John Wiley and Sons, NY, was then inserted into the SalI-BamHI site in a two step process. First, a 52 base pair duplex oligonucleotide. (The upper strand is referred to as SEQ ID NO. 1; the lower strand is referred to as SEQ ID NO. 2.)

```
5' TCGAGCTTGA CATTGTAGGA CTATATTGCT CTAATAAATT TGCGGCCGCT TG 3'
   CG AACTGTAACA TCCTGATATA ACGAGATTAT TTAAACGCCG GCGAACCTAG
``` that contained a consensus *E. coli* promoter sequence, a P1 c1 repressor sequence that overlapped the *E. coli* synthetic promoter, and a unique NotI site, was inserted into the SalI and BamHI site of the parent vector while regenerating the BamHI site but destroying the SalI site. Next, a 37 base pair duplex synthetic oligonucleotide. (The upper strand is referred to as SEQ ID NO. 3; the lower strand is referred to as SEQ ID NO. 4.)

Figure 1A:
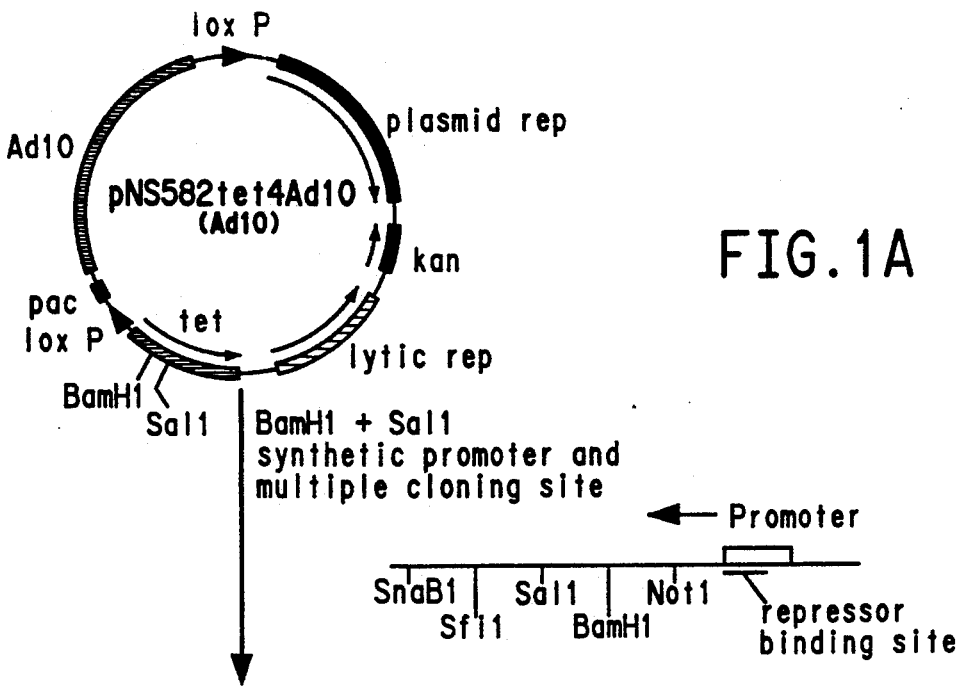
FIG. 1 A-B illustrates the steps involved in constructing the P1 positive selection vector.
Figure 1A:
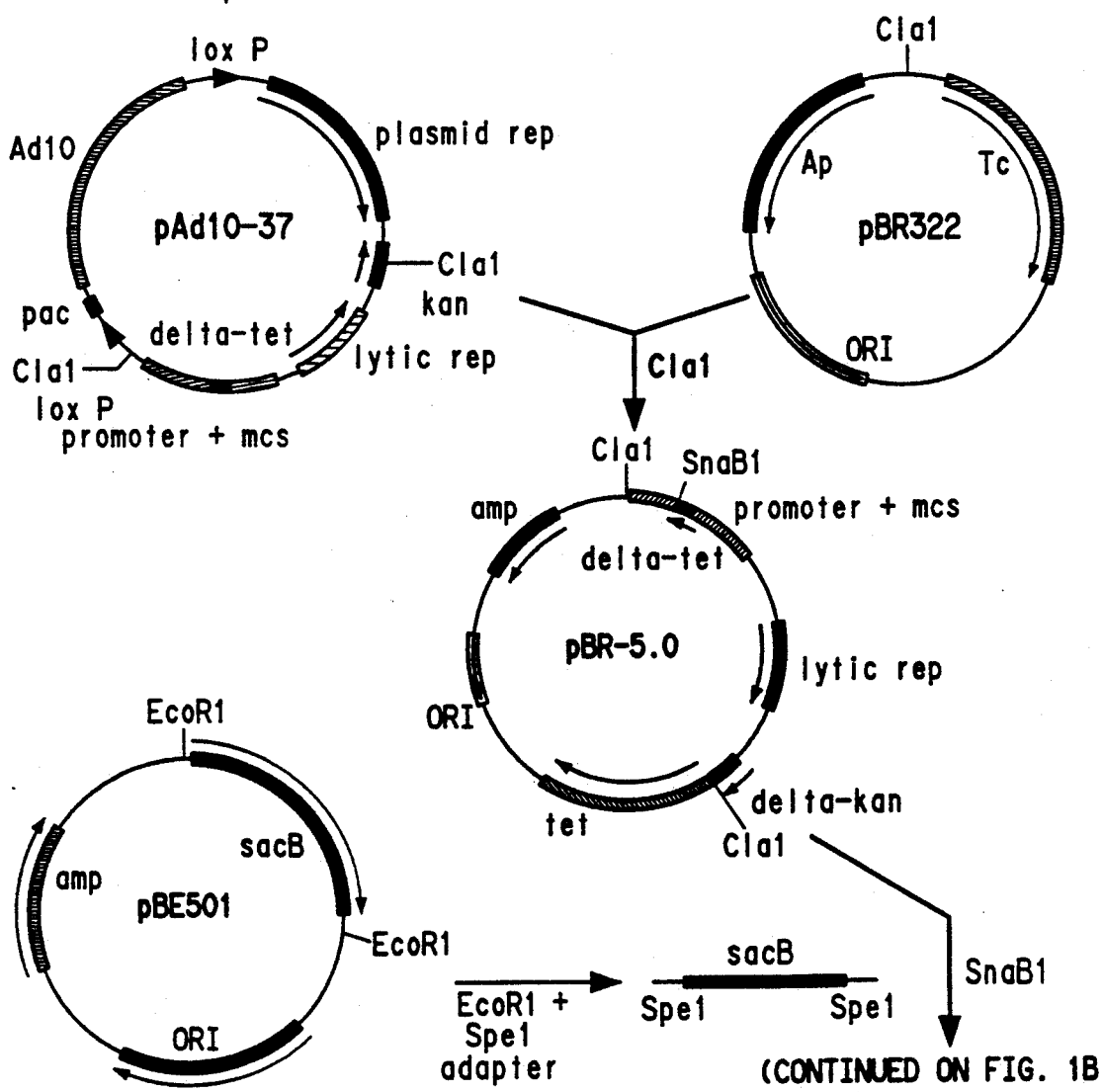
Figure 1B:
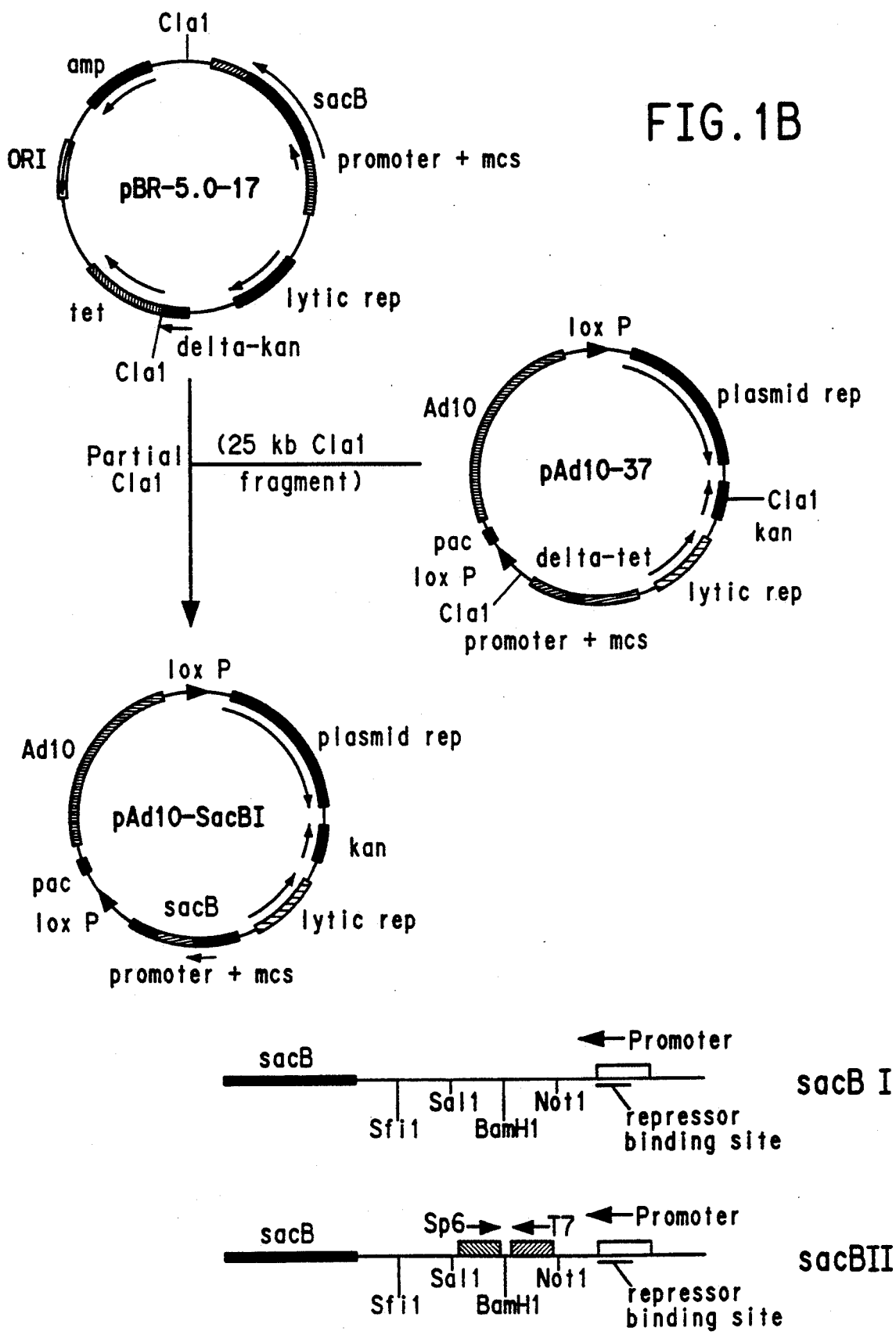

```
5' GGCCGCGGAT CCGTCGACGG CCAATTAGGC CTACGTA 3'
   CGCCTAG    GCAGCTGCCG GTTAATCCGG ATGCATCTAG
``` that contained a series of restriction sites (NotI, BamHI, SalI, SfiI, SnabI), was inserted into the first 52 base pair oligonucleotide using a NotI and BamHI digest. The NotI site was regenerated while the BamHI site was destroyed, leaving only a unique BamHI site located between the NotI and SalI sites. This series of genetic engineering steps created a P1 plasmid construct named pAd10-37 as shown in FIG. 1.

The next step in the construction of the P1 positive selection vector was to transfer a 5.0 kilobase (kb) ClaI DNA fragment which includes the pAd10-37 tetracycline gene with the promoter cassette insert, P1 lytic replicon, and part of the kanamycin gene into the ClaI site of pBR322. This was done to facilitate further experimental manipulations with a smaller plasmid (9 kb) rather than the 30 kb pAd10-37 plasmid. This plasmid was named pBR5.0. The pAd10-37 plasmid and the plasmid pBR322 were cut with the ClaI restriction enzyme. The 5.0 kilobase fragment was isolated and ligated into the ClaI site of pBR322.

A pUC plasmid (pBE501) (FIG. 1) containing the sacB gene from Bacillus amyloliouefaciens (gift from Vansantha Nagarajan, E. I. du Pont de Nemours and Company, CR&D Microbiology, U.S. patent application Ser. No. 07/376,474) was cut with restriction enzyme EcoRI which generated a 1.6 kb DNA fragment that contains the structural gene for sacB and the ribosome binding site but does not contain the endogenous sacB promoter. A 9 base pair EcoRI/SnaBI adapter. (The upper strand is referred to as SEQ ID NO. 5; the lower strand is referred to as SEQ ID NO. 6.)

```
5' CCACTAGTC      3'
   GGTGATCAGTTAA
``` that contains an internal unique SpeI restriction site was placed on each end of the 1.6 kb EcoRI DNA fragment. This was done so that the sacB structural gene was bordered by unique SpeI sites for easy physical identification and characterization of clones containing this insert. The modified 1.6 kb sacB fragment was ligated via blunt ends, into the unique SnaBI site of pBR5.0. DNA from this ligation reaction was transformed into E. coli strain DH5αIq (available from Bethesda Research Labs) that already contained a plasmid pACYC-P1c1, New England Biolabs. The pACYC-P1c1 plasmid contains the gene for the P1 c1 repressor protein, which is needed to prevent expression of the SacB gene, which even under permissive growth conditions (no sucrose in the media) exhibits a lethal phenotype. The P1 c1 protein is expressed by bacteriophage P1 to repress phage lytic functions during vegetative growth. This protein acts by binding an asymmetric recognition DNA sequence, usually in vicinity of an RNA polymerase promoter, Eliason and Sternberg, J. Mol. Biol. 198, 181-293 (1987). The lethal phenotype is probably due to the strong consensus E. coli promoter regulating the over expression of the SacB gene to produce a periplasmic SacB protein. The P1 c1 repressor protein is able to block expression of the sacB gene and allow replication of the otherwise lethal plasmid. Positive clones were identified by hybridization against the nick translated, radioactively labeled 1.6 kilobase fragment from plasmid pBE501. The correct plasmid construct was confirmed by physical mapping with diagnostic restriction enzymes and by the sensitivity of E. coli DH5αIq cells containing the plasmid to growth media containing sucrose, even in the presence of the P1 c1 repressor protein. This plasmid construct was named pBR5.0-17.

The next step in the construction of the P1 positive selection vector was to return the 6.6 kb ClaI fragment (previously 5.0 kb) of plasmid pBR5.0-17 to the parent pAd10-37 vector. DNA from plasmid pBR5.0-17 was subjected to a partial ClaI restriction digest, since there is a ClaI site in the sacB structural gene, and the 6.6 kb fragment was isolated and ligated to the 25 kb ClaI fragment of pAd10-37 DNA from this ligation reaction was transformed into E. coli strain DH5αIq that contained a lambda prophage expressing the P1 c1 gene. Positive clones were identified by restoration of the kanamycin resistant phenotype and by physical mapping via restriction enzyme digests This P1 vector was named pAd10-SacBI (FIG. 1). Initial characterization of bacterial cells containing this vector showed a lethal phenotype when grown on media containing sucrose. When DNA inserts were cloned into the unique BamHI site of pAd10-SacBI, cells containing these constructs were imparted with the ability to grow on media containing sucrose. This result demonstrated the utility and success of the P1 SacB positive selection vector.

To further increase the utility of the P1 SacB positive selection vector, a modification of the unique restriction site region (NotI, BamHI, SalI, and SfiI) was performed. The pAd10-SacBI vector was cut with the restriction enzymes NotI and SalI and a 56 base pair duplex synthetic oligonucleotide containing the promoter sequences for the T7 RNA polymerase and Sp6 RNA polymerase with a new BamHI site between the promoters was inserted into the NotI/SalI site at a position which directly bordered the unique BamHI cloning site, thus deleting the original unique BamHI site. (The upper strand is referred to as SEQ ID NO. 7; the lower strand is referred to as SEQ ID NO. 8.)

```
5' GGCCGCTAAT ACGACTCACT ATAGGGAGAG GATCCTTCTA TAGTGTCACC TAAATG    3'
       CGATTA TGCTGAGTGA TATCCCTCTC CTAGGAAGAT ATCACAGTGG ATTTACAGCT
```

Figure 2:
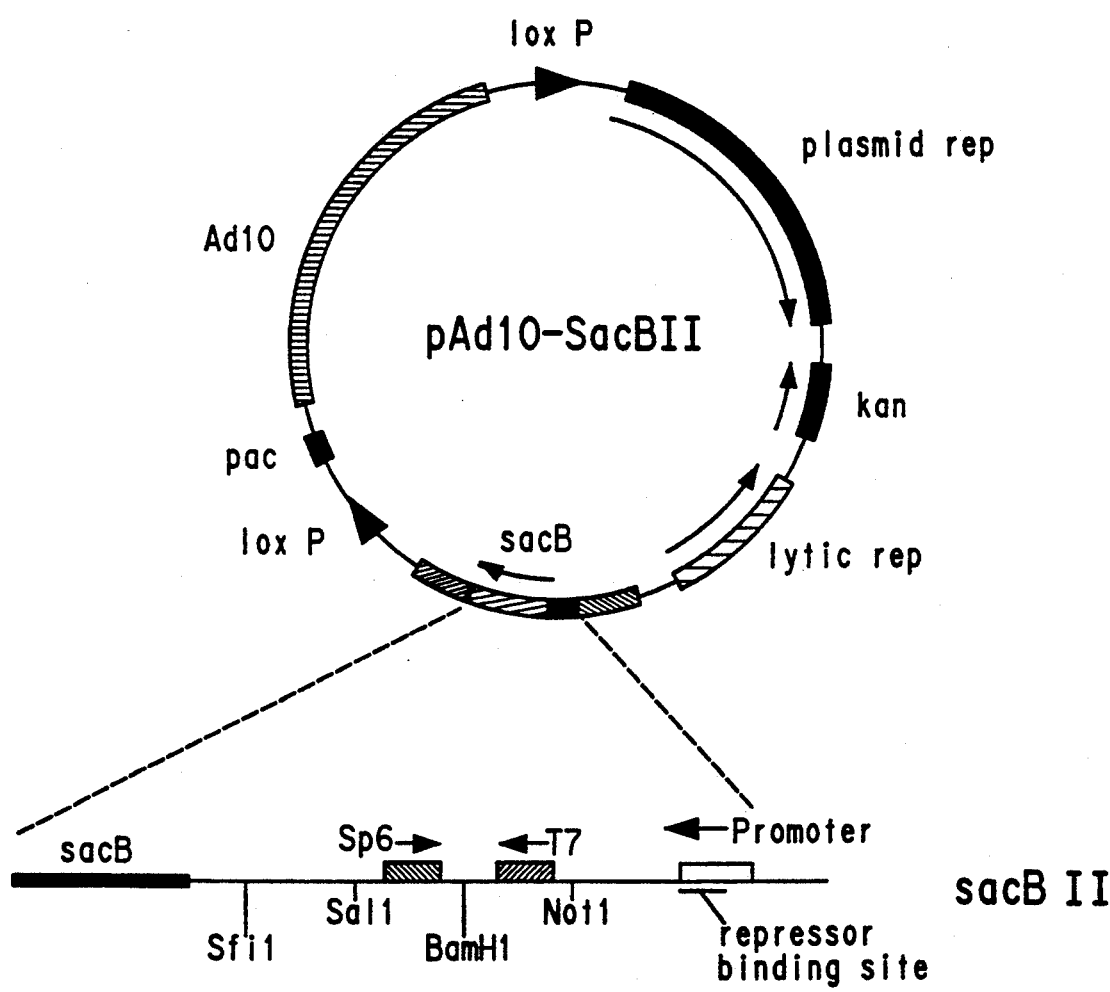
FIG. 2 illustrates the positive selection P1 cloning vector pAd10-SacBII.

The resulting fragment is referred to in SacBII (FIG. 1). The plasmid containing SacBII is referred to as pAd10-SacBII (FIG. 2). Confirmation of the correct plasmid construct was generated by restriction mapping and testing for the functional presence of the T7 and Sp6 promoters. We also observed that cells containing the pAd10-SacBII vector exhibited a "less" lethal phenotype when grown without the P1 c1 repressor in the absence of sucrose. This may be due to an "attenuator-like" effect produced by the insertion of the T7 and Sp6 promoter DNA sequences between the sacB structural gene and its synthetic promoter. This is the final version of the P1 positive selection vector and is named pAd10-SacBII. Experiments describing the utility of this vector are described below.

Construction of *E. coli* Host Strain Expressing the P1 c1 Repressor

To replicate the pAd10-SacBII vector the expression of levansucrase must be controlled. sacB gene expression under the control of the synthetic *E. coli* promoter gives a lethal phenotype in the absence of sucrose. We therefore constructed a host strain which expresses the P1 c1 gene at a high enough level to inhibit levansucrase expression. This was accomplished by constructing a bacteriophage lambda prophage that contains the P1 c1 repressor gene and inserting the construct into *E. coli* DP5αIq.

Phage lambda (imm21-P1:7Δ5b) is a phage containing a functioning P1 c1 repressor gene. It was generated from the starting phage lambda (dam15 b575 b529 attλ+imm21) in which P1 EcoRI fragment 7 (O'Brien, Genetic Maps, Cold Spring Harbor Press, Cold Spring Harbor, N.Y. 1990) was cloned at lambda map coordinate 65.8. EcoRI-7 contains the P1 cre gene, the P1 loxP site, and the p1 c1 repressor gene, Sternberg et al., J. Mol. Biol. 187, 197–212 (1986). Deletion mutants of the above starting phage were isolated and the location of the deleted DNA determined by restriction mapping, as described in Eliason and Sternberg, J. Mol. Biol. 198, 281–293 (1987). One mutant, designated lambda (imm21-P1:7Δ5b), contained a contiguous deletion of DNA extending from the attλ site into the cloned P1 sequences. P1 BamHI-EcoRI fragment 8* (cre containing EcoRI-BamHI fragment from P1 EcoRI fragment 7) was completely removed and part of P1 BamHI fragment 9 was removed. In vivo loxP-cre reactions indicated that this lambda deletion mutant construct was loxP-, cre-. Further experiments showed that an *E. coli* lysogen containing this prophage synthesized functional P1 c1 repressor protein. This strain is called NS3607. These results indicate that the Δ5b deletion terminates between P1 loxP and the P1 c1 gene in the P1 BamHI fragment 9 (O'Brien, supra). The *E. coli* DH5αIq (P1 c1) was used as a host strain to prepare pAd10-SacBII plasmid DNA for cloning experiments described below.

Preparation of pAd10-SacBII DNA

Significant care must be given in the preparation of pAd10-SacBII DNA. Vector DNA is prepared by the cesium chloride density gradient method as described by Godson and Vapnek, Biochim. Biophys. Acta. 299, 516–522 (1973). The observation that bacteria containing the SacBI vector expressed a lethal phenotype even in the absence of sucrose in the media resulted in a careful analysis of cesium chloride prepared SacBI DNA. Restriction analysis showed that a significant portion of the vector DNA was deleted in the region containing the sacB gene. When this DNA was transformed into *E. coli* DH5αIq and the bacteria grown on agar plates containing 5% sucrose, only bacteria that contained the population of SacBI plasmids that had a deletion grew well. This result significantly compromises the utility of the P1 positive selection system since it generated a large background of clones not containing DNA inserts, exactly what the SacB positive selection was supposed to eliminate. This problem was overcome by the construction of the pAd10-SacBII vector which contains an extra 43 base pairs of DNA (T7 and Sp6 RNA promoters) between the sacB structural gene and its synthetic promoter. *E. coli* DH5αIq (P1 c1) NS3607 that contained this vector (SacBII) did not display the lethal phenotype in the absence of sucrose in the growth media. Still, careful analysis of vector DNA is necessary when preparing large amounts of DNA for cloning experiments. This is achieved by restriction analysis of vector DNA and by transformation of competent *E. coli* cells with vector DNA to determine the percentage of the plasmid population which are sucrose resistant.

Restriction Digest of pAd10-SacBII DNA

Vector arms are prepared by a sequential double restriction digest of the SacBII DNA. Three micrograms of vector DNA was incubated with the restriction enzyme ScaI (New England Biolabs) as per manufacture's instructions, in a 30 microliter reaction. The reaction was incubated at 37° C. for one hour. The reaction volume was increased to 50 microliters with water, BamHI restriction buffer and 1 microliter of BamHI. The reaction was incubated for 10 minutes at 37° C. The digest reaction was then extracted with one volume phenol, one volume chloroform-isoamyl alcohol (24:1) saving the aqueous layer each time. The DNA was precipitated with two to three volumes of ice cold ethanol and 0.3M sodium acetate and the mixture placed on ice for 30 minutes. The DNA was collected by centrifugation in a microcentrifuge at room temperature for 20 minutes, washed with 0.5 ml of 75% ethanol and the pellet air dried. The DNA pellet was resuspended in 20 microliters of TE buffer (10 mM Tris (pH 8.0) 1 mM EDTA).

Preparation and Analysis of High Molecular Weight Insert DNA for Cloning into pAd10-SacBII There are many protocols for the preparation of genomic DNA that can be used in the P1 cloning system. This depends upon the organism, tissue or cell type in question. The pAd10-SacBII vector was tested on DNA prepared from human lymphoblastoid cell line 697 as described by Sternberg, U.S. patent application No. 07/397,071, (1989) and Sternberg et. al., The New Biol. 2, 151–162 (1990). Briefly, DNA was isolated from lysed cells and fractionated on a 10–40% sucrose gradient After dialysis, 0.5 ml of the large molecular weight DNA was incubated with 4 units of Sau3I restrictive enzyme and restriction buffer minus magnesium, overnight at 4° C. This ensured adequate mixing of the Sau3I restriction enzyme with the viscous genomic DNA. Digestion was initiated by adding magnesium chloride to 10 mM and aliquots were removed at 10 different time points and the reaction terminated by adding EDTA to 20 mM and heating at 70° C. for 15 minutes.

The Sau3I partial digest of genomic DNA was analyzed by removing 10% of each time point fraction and subjecting the DNA to agarose field inversion pulse gel electrophoresis. The DNA was fractionated via electrophoresis to resolve fragment sizes between 20 and 200 kb by a 1% agarose gel in 0.5×'s TBE buffer (89 mM Tris pH 8,0, 89 mM borate, 2 mM ethylene diamine tetraacetic acid (EDTA)), for 4 hours at 180 volts with a 0.6 sec. forward, 0.2 sec. reverse, and ramp of 20, pulse conditions. The gel was stained with ethidium bromide and DNA visualized with uv fluorescence. Those aliquots that contained digested genomic DNA fragments in the 70 to 100 kb range were used as substrate for cloning into the pAd10-SacBII vector.

Ligation and Packaging of SacBII Vector and Genomic Insert DNA

The ligation of the SacBII vector arms to genomic DNA and its subsequent in vitro packaging into P1 capsids has been described in detail in Sternberg, Proc. Natl. Acad. Sci. USA 87, 103-107 (1990) and Sternberg, U.S. patent application No. 07/397,071. 0.2 micrograms ScaI/BamHI digest SacBII vector arms were incubated with Sau3A digested genomic DNA or with TE buffer (no insert control experiment) in ligase buffer (50 mM Tris pH 7.5, 10 mM MgCl$_2$, 10 mM dithiothreitol, 50 mg/ml bovine serum albumin) for 30 minutes at 37° C. DNA ligase and ATP (to 2 mM) were then added and the reaction incubated at 16° C. overnight. The ligation reaction was then heated at 65° C. for 5 minutes and added to the first part of the two stage in vitro P1 packaging reaction. The stage 1 extract is a bacteriophage P1 lysate that contains the enzymes needed to cleave the pac site of the P1 cloning vector. The stage 2 extract is a bacteriophage P1 lysate that contains the components (phage capsids and tails) necessary to form an infectious phage particle. The stage 1 reaction was incubated for 15 minutes at 30° C. and then transfered to the stage 2 reaction, which was incubated for 20 minutes at 30° C. The final reaction was diluted to a total volume of 180 microliters with TMG buffer (10 mM Tris pH 8.0, 10 mM MgCl$_2$, 0.1% gelatin) plus pancreatic DNase (10 ug/ml). Fifteen microliters of chloroform were added to the P1 packaging reaction, and then stored at 4° C.

Growth and DNA Preparation of P1 Clones Containing High Molecular Weight DNA inserts A 10 to 20 microliter aliquot from each P1 packaging reaction was added to 0.1 ml of mid-log phase, concentrated (10×), E. coli bacteria containing the cre recombinase (strains NS3145 or NS3529). After a 10 minute incubation at 37° C., one ml of L broth was added to the phage/cell mixture and then incubated for 30-60 minutes at 37° C. with shaking. The infected cells were pelleted in a microcentrifuge and then resuspended in 0.15 ml of L broth and then spread on L agar plates that contained 25 ug/ml kanamycin with or without 5% sucrose. The plates were incubated at 37° C. overnight. Kanamycin and kanamycin/sucrose resistant colonies were recorded.

P1 clone plasmid DNA was prepared by picking a single bacterial colony with a 50 microliter capillary pipet and adding it to 10 ml of L broth containing 25 ug/ml kanamycin. The cells were grown at 37° C. for about 3 hours (early log phase) and IPTG was added to a final concentration of 1 mM. The cells were grown for another 5 hours and then pelleted. DNA was prepared by the alkaline lysis procedure of Birnboim et al., Nucl. Acids Res. 7, 1513-1523 (1979). Plasmid DNA was resuspended in 40 microliters of TE buffer and 0.4 micrograms RNase.

Characterization of Genomic Insert DNA from pAd10-SacBII P1 Clones

The pAd10-SacBII vector allows the characterization of insert DNA by use of the novel rare cutting restriction sites which border the BamHI cloning site and by the ability to make RNA probes from either or both ends of the genomic insert via the T7 and Sp6 promoters. Physical mapping and size characterization of cloned insert DNA is facilitated by the ability to isolate the SacBII vector sequence away from the genomic DNA. Chromosome walking and DNA sequencing of cloned inserts is achieved by the utilization of the unique promoter sequences. Those skilled in the art will recognize that these features have been successfully utilized in plasmid and cosmid cloning as described in Melton et al., Nucl. Acids Res. 12, 7035-7056 (1984) and Wahl et al., Proc. Natl. Acad. Sci. USA 84, 2160-2164 (1987).

Physical characterization of P1 clones was carried out by restriction enzyme digestion. Each digestion reaction contains 13 microliters of plasmid DNA from a particular p1 clone, 1.5 microliters of restriction buffer, and 1.0 microliter of each restriction enzyme (either BglII, NotI or NotI and SalI). The restriction digest was performed at 37° C. for 2 hours, then subjected to a phenol/chloroform extraction, and air dried to remove excess chloroform. If the volume was too large an ethanol precipitation step was also included and the DNA resuspended in 15 microliters of TE buffer. The DNA was then analyzed on a 1% agarose pulse field inversion gel electrophoresis in 0.5× TBE buffer using pulse conditions of 0.6 sec. forward, 0.2 sec. reverse, ramp 20 at 120 volts for 15 hours. The gel was then stained with ethidium bromide and the DNA visualized by uv fluorescence.

EXAMPLE 1

Transformation Efficiencies of Uncut and Cut/ligated pAd10-SacBII

To determine the efficiency of the positive selection feature of the pAd10-SacBII vector, DNA transformation experiments were carried out. After a cesium chloride banded DNA preparation of the SacBII vector had been generated, the DNA was analyzed by a restriction digest with BglII, SpeI, and BamHI/ScaI. The results showed that the correct size DNA fragments were produced with no apparent rearrangements observed. Two hundred nanograms of pAd10-SacBII from two different DNA preparations was transformed into E. coli strains NS3145 (cre+) and DH5Iq (cre−) as described by Maniatis et al., Molecular cloning: A Laboratory Manual (Cold Spring Harbor Laboratory, Box 100, Cold Spring Harbor, N.Y. (1982). Strain NS3145 maintains the SacBII vector as a single copy plasmid due to cre mediated lox-lox recombination. Strain DH5Iq maintains the SacBII vector as a multicopy plasmid. This difference is important since the sacB positive selection function must work with only one copy of the gene present per bacterial cell. The transformed cells were plated on L agar plates containing kanamycin or kanamycin/5% sucrose and grown overnight at 37° C. The number of resistant colonies were counted (or estimated) and are shown in part A of Table 1. The same pAd10-SacBII DNA (100 ng each) was cut with the restriction enzymes BamHI, SalI, SacI/BamHI or ScaI/SalI, extracted with phenol/chloroform, ethanol precipitated and resuspended in TE buffer (as described previously). The digested DNA was then placed in a ligation reaction, incubated overnight at 16° C., and transformed into E. coli strains NS3145 and DH5Iq (as described above). Kanamycin and kanamycin/sucrose resistant colonies were recorded and are shown in part B of Table 1.

TABLE 1

| | DNA Transformation Efficiencies of pAd10-SacBII | | | |
|---|---|---|---|---|
| | NS3145 (cre+) | | DH5Iq (cre−) | |
| DNA | Kan$^r$ | Sucrose$^r$ | Kan$^r$ | Sucrose$^r$ |
| A) | | | | |
| uncut #1 | ~10,000 | 6 | ~10,000 | 2 |
| uncut #2 | ~10,000 | 7 | ~10,000 | 7 |
| B) | | | | |
| uncut | 361 | 2 | 405 | 0 |
| BamHI | 135 | 6 | 90 | 5 |
| SalI | 246 | 5 | 222 | 3 |
| ScaI/BamHI | 56 | 7 | 9 | 13 |
| SacI/SalI | 107 | 7 | 34 | 9 |

The results in part (A) show that the positive selection efficiency, calculated as the number of kan-r colonies divided by the number of kan/sucrose-r colonies, for the uncut SacBII vector was approximately 1000 fold. This was true whether the sacB gene was at single (NS3145) or multicopy (DH5Iq). These results indicate that only a small proportion of the pAd10-SacBII DNA contains an inactive sacB gene or nonfunctional synthetic promoter. This "background" population is most likely due to single base mutations in the sacB structural gene and promoter region which change the expression of levansucrase either quantitatively or qualitatively, thus allowing growth on media containing sucrose. The results from part (B) indicate that molecular biological manipulations (restriction digestion and ligation reactions and phenol/chloroform extractions) do have an impact on the efficiency of the SacB positive selection system. The transformation efficiency was decreased even for the uncut DNA, although less DNA (100 ng as opposed to 200 ng) was used for each strain transformed. The positive selection efficiency was approximately 200 to >400 fold. This number dropped somewhat when the pAd10-SacBII was cut at the unique BamHI and SalI sites between the sacB structural gene and the synthetic promoter. Since a ligation step is necessary to achieve a functional pAd10-SacBII molecule, it is possible that plasmid dimers can form which inactivate the sacB gene by a head to head or tail to tail arrangement. These plasmid dimers would still be kan-r but would no longer show sucrose sensitivity. When the SacBII vector was cut to generated "arms" via the ScaI/BamHI or SalI double digest, transformation efficiencies were markedly decreased, this is not surprising since ScaI creates a blunt end which is recalcitrant to ligation. Interestingly the positive selection efficiency was very poor (2 to 5 fold). This may be due to the fact that under these conditions most of the kan-r colonies are from generated plasmids via aberrant ligation products that inactivate the sacB gene hence giving a sucrose resistant phenotype.

EXAMPLE 2

DNA Packaging and Positive Selection Efficiencies of pAd10-SacBII

To determine how well the positive selection system of the SacBII vector would perform during the construction of a genomic library, the following model experiment was done. Four micrograms of pAd10-SacBII DNA was cut with the appropriate restriction enzyme (as described above) at 37° C. for 3 hours. DNA was extracted with phenol/chloroform and then ethanol precipitated. Some samples were then treated with calf intestinal phosphatase (CIP) (see Table 2, part (A) below) by resuspending the DNA in 50 microliters of 50 mM Tris (pH 8.0), 0.1 mM EDTA. Calf intestinal phosphatase was added to a final concentration of 0.01 units and the reaction incubated at 37° C. for 1 hour. The CIP reaction was extracted with phenol/chloroform, ethanol precipitated and resuspended in 20 microliters of TE buffer. The cut SacBII vector DNA was then placed in a ligation reaction in the absence of foreign DNA, under the following conditions: ~3 ug vector DNA (18 ul), 3 ul 10× ligase buffer, 2 ul 25 mM ATP, 1.5 ul T4 DNA ligase, 5 ul TE buffer. The DNA was first heated at 70° C. for 2 minutes and then the rest of the ligation reaction added and incubated at 16° C. overnight. The ligation reaction was then heated at 70° C. for 3 minutes and added to the two stage P1 in vitro packaging reaction as described previously.

In part (B) of Table 2, partially Sau3A digested human DNA was used in the ligation reaction with the pAd10-SacBII vector. Two hundred nanograms of vector DNA was digested with ScaI and BamHI and added to Sau3A partially digested human genomic DNA (as described previously) and incubated at 37° C. for 30 minutes. Ligation reactions were set up as follows: 1.5 ul (200 ng) vector DNA, 15 ul (~1 ug) human genomic DNA, 2 ul 10× ligase buffer, 1 ul 25 mM ATP, 1 ul T4 DNA ligase and incubated overnight at 16° C. Tris-EDTA buffer was substituted for the vector control reaction. Three different time fractions (6, 8, and 10 minutes) of the human genomic Sau3A partial digest were used. The ligation reactions were heated for 3 minutes at 70° C. and added to the P1 in vitro packaging reaction as described previously. The number of kanamycin and kanamycin/sucrose resistant colonies were recorded and are presented in Table 2.

TABLE 2

| | DNA Packaging and Positive Selection Efficiency of pAd10-SacBII | | |
|---|---|---|---|
| | | NS3529 (cre+) | |
| Vector DNA | Insert DNA | Kan$^r$ | Sucrose$^r$ |
| A) | | | |
| uncut | none | ~2000 | 1 |
| BamHI | none | ~1500 | 200 |
| ScaI | none | ~2000 | 0 |
| BamHI (CIP) | none | ~250 | 5 |
| ScaI (CIP)/BamHI | none | ~1500 | 42 |
| ScaI/BamHI (CIP) | none | ~350 | 28 |
| B) | | | |
| ScaI/BamHI | none | 800 | 8 |
| scaI/BamHI | Hu-6" | 686 | 516 |
| ScaI/BamHI | Hu-8" | 518 | 328 |
| ScaI/BamHI | Hu-10" | 574 | 418 |

These results show that the SacBII vector significantly decreases the amount of kan-r colonies when plated on media containing 5% sucrose. In part (A) of Table 2 the SacBII vector was cut with restriction enzymes BamHI or ScaI and then religated. Interestingly, only the BamHI cut increased the number of sucrose resistant colonies while the ScaI cut, which is distant from the sacB structural gene, did not. This data is in accord with the data from Table 1 which showed an increase in the number of sucrose resistant colonies when the region between the saB gene and its promoter were manipulated via restriction digest and ligation. Phosphatase treatment with CIP did decrease the total number of kanamycin resistant colonies when the BamHI site was treated. Also, CIP treatment improved the ratio of suctose-r colonies to kan-r colonies. Part (B) of Table 2 reflects the experimental conditions in which genomic libraries can be generated using the P1 cloning system. As stated previously, one problem with the old P1 cloning vector (pAd10) was the number of kan-r colonies generated with no insert. As can be seen from the control ScaI/BamHI with no insert DNA the number of kan-r colonies are decrease 100 fold when plated on media containing sucrose. This result demonstrates that the SacBII vector greatly reduces the contribution of potential "no-insert" containing clones during a genomic cloning experiment. This result is further supported by the data generated when genomic DNA is added to cut SacBII vector during the ligation reactions. The number of sucrose-r colonies is increased over 60 fold in the Hu-6" reaction. Also, the relative number of sucrose-r colonies divided by kan-r colonies is greatly decreased indicating that most of the SacBII vector has productively ligated to genomic DNA fragments. It is that fraction of "insert-less" clones which grow on the kan-r plate but not on the sucrose-r plate that the SacBII positive cloning system was designed to select against. The following example demonstrates that the sucrose-r clones do contain genomic DNA while some of the kan-r clones do not.

EXAMPLE 3

Analysis and Characterization of SacBII High Molecular Weight Human Clones

To demonstrate that the pAd10-SacBII sucrose resistant colonies actually contain genomic DNA inserts, DNA was prepared from a number of colonies from both the kan-r and sucrose-r populations generated in the packaging experiment described in Example 2. These clones were analyzed via restriction mapping with BglII/XhoI and fractionation on agarose gel electrophoresis. The SacBII-human DNA's were also characterized by NotI restriction digest and fractionation via pulse field inversion gel electrophoresis.

DNA was prepared (as described above) from 64 colonies from the kanamycin/5% sucrose plates and 12 colonies from the kanamycin plates from the Hu-6" and Hu-8" reactions described in Example 2. Thirteen microliters of DNA was digested with BglII and XhoI at 37° C. for 1 hour. The reaction was stopped by heating at 70° C. for 5 minutes in the presence of stop dye buffer (6× =0.25% bromophenol blue, 0.25% xylene cyanol, 40% (w/v) sucrose in water) an the DNA fragments were then fractionated on a 1% agarose gel for 12 hours at 20 volts in 1× TBE buffer. The gels were stained with ethidium bromide and DNA visualized by uv fluorescence. Results show that almost all (>95% of the sucrose-r clones contain a genomic DNA insert but that many of the kan-r clones (~66%) do not contain DNA inserts. This difference is due to the positive selection aspect of the pAd10-SacBII vector.

Figure 3:
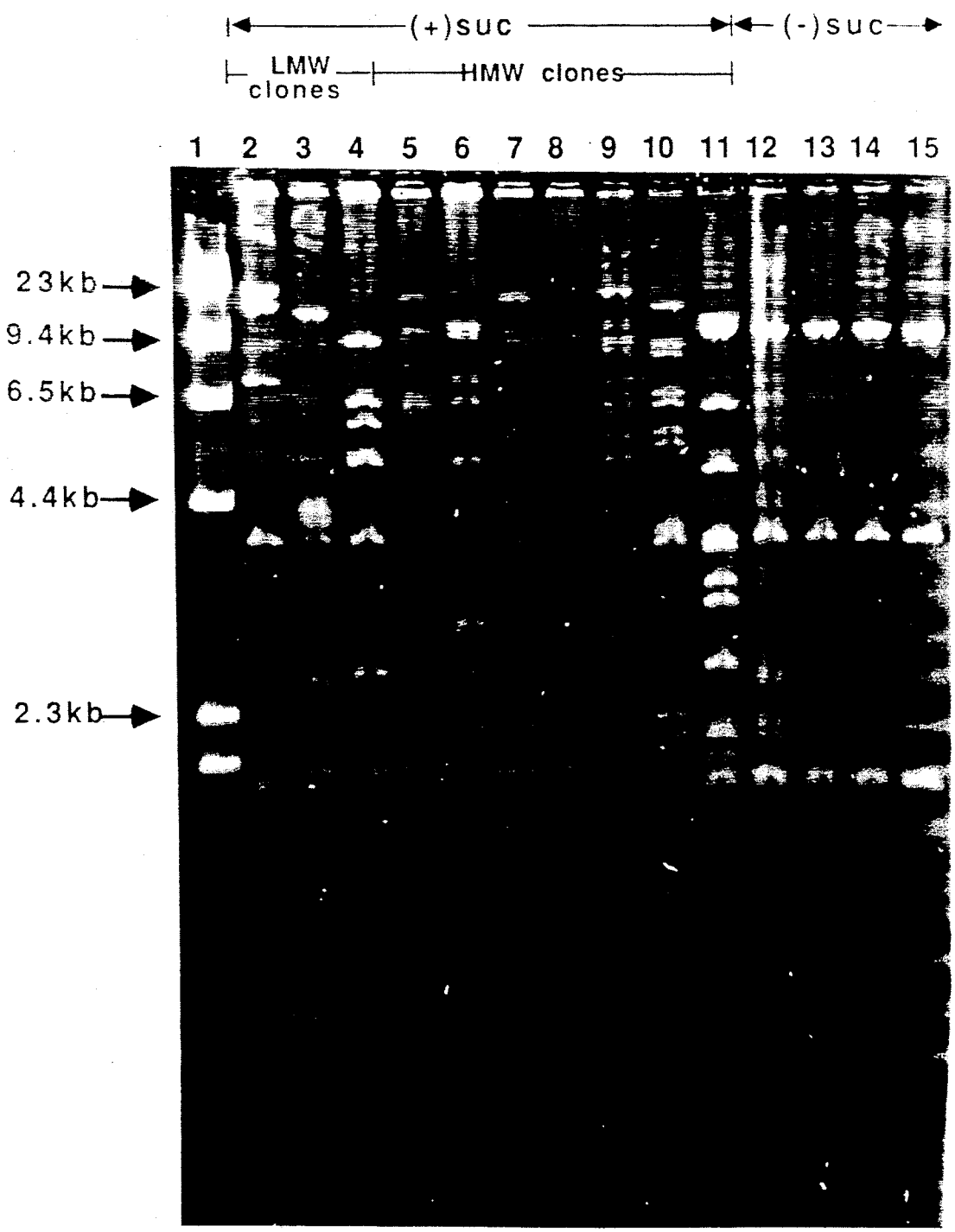
FIG. 3 illustrates a BglII/XhoI restriction digest of pAd10-SacBII-human clones from (sucrose) and (no sucrose) agar plates.

A photograph of a gel that is a composite of a representative portion of the sampled colonies is presented in FIG. 3. Lane 1 contains molecular weight markers, lanes 2-11 contain DNA from colonies derived from the kanamycin/sucrose agar plates, lanes 12-15 contain DNA from colonies from the kanamycin plates. The DNA from clones in lanes 2-4 are SacBII vectors that contain relatively small genomic inserts. Lanes 5-11 are SacBII clones that contain large molecular weight human genomic inserts. Lanes 12-15 contain DNA with no genomic DNa inserts and reflect the DNA fragments generated from the pAd10-SacBII vector after it has gone through cre mediated lox-lox recombination. Background fragments are due to the presence of the F' plasmid that the lacIq gene recombinase in *E. coli* strain NS3145.

Figure 4:
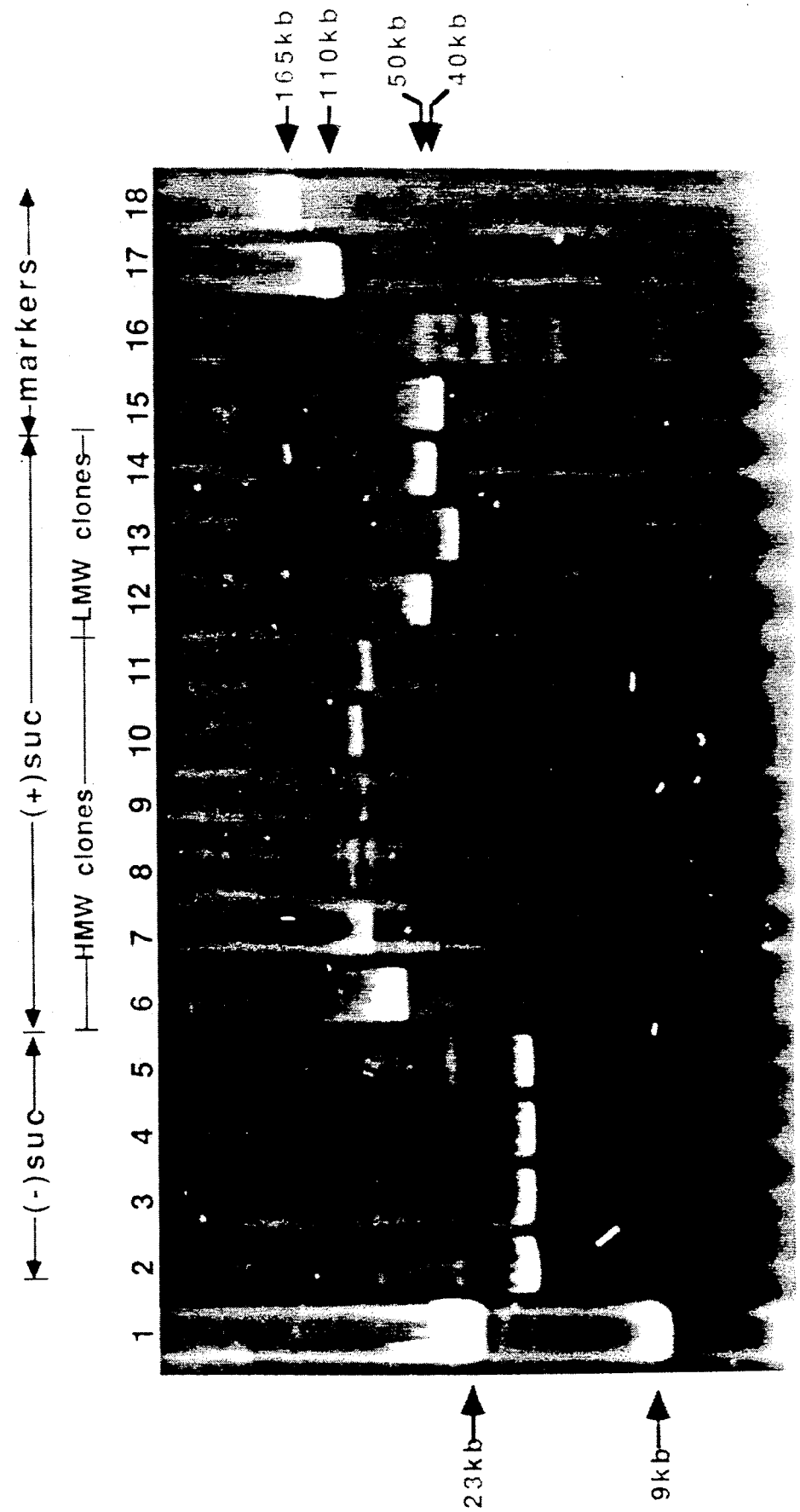
FIG. 4 illustrates the ability to linearize and size characterize a P1 clone using the rare restriction site NotI.

To further characterize the SacBII P1 clones DNA from a portion of the clones presented in FIG. 3 were subjected to a NotI restriction digest and then fractionated on a 1% agarose field inversion gel electrophoresis (methodology as described above). A photograph of this gel is presented in FIG. 4. Lanes 1, 15-18 are molecular weight markers, lanes 2-5 are clones from kanamycin plates (no sucrose), lanes 6-14 are clones from the kanamycin/sucrose agar plates. The clones from the no sucrose plates contain no genomic DNA inserts and the size of the SacBII fragment after lox-lox recombination is about 18 kb. The clones from the plus sucrose plates contain DNA inserts of two general sizes. The large molecular weight clones range in size from 75 to 100 kb. The low molecular weight clones are in the 30 to 50 kb range. DNA's in lanes 2-8 are from strain NS3145 and those in lanes 9-14 are from strain NS3529. The smaller NotI fragment in lane 8 is from the F'lacIq plasmid in strain NS3145 and the larger fragment is from the SacBII-human plasmid. These results demonstrate the power of rare restriction site mapping (in this case NotI) in the analysis of P1 clones using the new pAd10-SacBII vector.

From the foregoing description, one skilled in the art can easily ascertain the essential characteristics of this invention and without departing from the spirit and scope thereof, can make various modifications and changes of the invention to adapt to various uses and conditions.

What is claimed is:

1. A vector comprising a positive selection cassette for use in an *Escherichia coli* host, said cassette comprising, (a) a SacB gene from *Bacillus amyloliquifaciens*, the expression of which is lethal to a *Escheriehia coli* host;

(b) SfiI and SalI restriction sites upstream of the SacB gene;

(c) Sp6 and T7 RNA polymerase promoters bordering a BamHI restriction site between them and located upstream of the SalI restriction site;

(d) a NotI restriction site upstream of the T7 promoter;

(e) a consensus *Escherichia coli* promoter which controls expression of the SacB gene and which is upstream of the NotI restriction site;

(f) a P1c1 repressor protein binding site overlapping said consensus *Escherichia coli* promoter for the binding of a P1c1 protein and the control of said consensus promoter;

(g) a P1 lytic replicon for the amplification of the vector under derepression; and (h) a P1 plasmid replicon for maintaining single copy number of the vector under conditions of lytic replicon repression, wherein lethal expression of the SacB gene in the *Escherichia coli* host can be blocked either by expression of a P1c1 repressor gene or by cloning a large molecular weight DNA fragment into the GamHI site between the Sp6 and T7 RNA polymerase promoters.

2. An *Escherichia coli* host cell comprising the vector of claim 1.

3. A method of positive selection of nucleic acid clones, comprising:
   (a) cloning a large molecular weight DNA fragment into the vector of claim 1 at the cloning site;
   (b) inserting the vector into an appropriate host cell; and
   (c) growing the host cell under nonrepressed conditions.

4. Plasmid pAd10-SacBII having ATCC designation 68505.

5. Plasmid pAd10-SacBI having ATCC designation 68504.

* * * * *